(12) United States Patent
Zhang et al.

(10) Patent No.: US 9,949,719 B2
(45) Date of Patent: Apr. 24, 2018

(54) BREAST IMAGING METHOD AND SYSTEM

(71) Applicant: GENERAL ELECTRIC COMPANY, Schenectady, NY (US)

(72) Inventors: Zhipeng Zhang, Santa Clara, CA (US); Cynthia Elizabeth Landberg Davis, Niskayuna, NY (US); Weston Blaine Griffin, Niskayuna, NY (US); Ying Mao, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 156 days.

(21) Appl. No.: 14/572,416

(22) Filed: Dec. 16, 2014

(65) Prior Publication Data

US 2016/0166234 A1 Jun. 16, 2016

(51) Int. Cl.
| | |
|---|---|
| *A61B 5/00* | (2006.01) |
| *A61B 8/00* | (2006.01) |
| *A61B 8/08* | (2006.01) |
| *A61B 8/14* | (2006.01) |
| *A61B 6/02* | (2006.01) |

(Continued)

(52) U.S. Cl.
CPC ............ *A61B 8/4416* (2013.01); *A61B 6/025* (2013.01); *A61B 6/0414* (2013.01); *A61B 6/4417* (2013.01); *A61B 6/502* (2013.01); *A61B 8/0825* (2013.01); *A61B 8/14* (2013.01); *A61B 8/403* (2013.01); *A61B 8/4209* (2013.01); *A61B 8/4461* (2013.01); *A61B 8/54* (2013.01); *A61B 8/429* (2013.01); *A61B 8/4281* (2013.01)

(58) Field of Classification Search
CPC ......... A61B 8/4416; A61B 6/502; A61B 6/02; A61B 8/13; A61B 8/54; A61B 8/42; A61B 8/4483
See application file for complete search history.

(56) References Cited

U.S. PATENT DOCUMENTS

| | | |
|---|---|---|
| 4,943,986 A | 7/1990 | Barbarisi |
| 5,335,257 A | 8/1994 | Stunberg |

(Continued)

FOREIGN PATENT DOCUMENTS

| | | |
|---|---|---|
| WO | 9802094 A1 | 1/1998 |
| WO | 2013171671 A1 | 11/2013 |

OTHER PUBLICATIONS

Sinha et al., "Multi-Modality 3D Breast Imaging With X-Ray Tomosynthesis and Automated Ultrasound", Conference Proceedings IEEE Engineering Medicine and Biology Society, pp. 1335-1138, Aug. 23-26, 2007.

(Continued)

*Primary Examiner* — Joel Lamprecht
(74) *Attorney, Agent, or Firm* — Pabitra K. Chakrabarti

(57) ABSTRACT

An ultrasound scan probe and support mechanism are provided for use in a multi-modality mammography imaging system, such as a combined tomosynthesis and ultrasound imaging system. In one embodiment, the ultrasound components may be positioned and configured so as not to interfere with the tomosynthesis imaging operation, such as to remain out of the X-ray beam path. Further, the ultrasound probe and associated components may be configured to as to move and scan the breast tissue under compression, such as under the compression provided by one or more paddles used in the tomosynthesis imaging operation.

18 Claims, 15 Drawing Sheets

(51) Int. Cl.
*A61B 6/00* (2006.01)
*A61B 6/04* (2006.01)

(56) References Cited

U.S. PATENT DOCUMENTS

| | | |
|---|---|---|
| 5,474,072 A | 12/1995 | Shmulewitz |
| 5,775,337 A | 7/1998 | Hauger et al. |
| 5,840,022 A | 11/1998 | Richter |
| 5,938,613 A | 8/1999 | Shmulewitz |
| 6,102,866 A | 8/2000 | Nields et al. |
| 6,574,499 B1 | 6/2003 | Dines et al. |
| 6,846,289 B2 | 1/2005 | Besson et al. |
| 6,975,701 B2 | 12/2005 | Galkin |
| 7,349,521 B2 | 3/2008 | Al-Khalidy et al. |
| 7,489,761 B2 | 2/2009 | Defreitas et al. |
| 7,556,602 B2 | 7/2009 | Wang et al. |
| 7,656,993 B2 | 2/2010 | Hoernig |
| 7,742,558 B2 | 6/2010 | Mertelmeier |
| 7,792,244 B2 | 9/2010 | Defreitas et al. |
| 7,822,457 B2 | 10/2010 | Lokhandwalla et al. |
| 7,849,761 B2 | 12/2010 | Forslund |
| 7,916,918 B2 | 3/2011 | Suri et al. |
| 8,192,361 B2 | 6/2012 | Sendai |
| 8,592,772 B2 | 11/2013 | Stein et al. |
| 8,787,522 B2 | 7/2014 | Smith et al. |
| 2003/0149364 A1 | 8/2003 | Kapur et al. |
| 2004/0181152 A1 | 9/2004 | Zhang et al. |
| 2005/0089205 A1 | 4/2005 | Kapur et al. |
| 2005/0265518 A1 | 12/2005 | Aubel |
| 2009/0129556 A1 | 5/2009 | Ahn |
| 2009/0175408 A1 | 7/2009 | Goodsitt et al. |
| 2011/0087098 A1 | 4/2011 | Fischer et al. |
| 2012/0029344 A1 | 2/2012 | Nakayama |
| 2012/0150034 A1 | 6/2012 | Defreitas et al. |
| 2013/0116570 A1* | 5/2013 | Carson ............... A61B 8/4281 600/459 |
| 2013/0129039 A1 | 5/2013 | Defreitas et al. |
| 2014/0121520 A1 | 5/2014 | Wang et al. |
| 2014/0135623 A1* | 5/2014 | Manak ............... A61B 8/4416 600/427 |
| 2014/0180082 A1 | 6/2014 | Evans et al. |

OTHER PUBLICATIONS

Kapur et al., "Combination of Digital Mammography With Semi-Automated 3D Breast Ultrasound", Technology in Cancer Research & Treatment, vol. No. 3, Issue No. 4, pp. 325-334, Aug. 16, 2010.
"Frost & Sullivan: Multi-modality Breast Imaging Systems Spur Innovation in Europe", ITN Online, pp. 1-13, Aug. 27, 2014.
PCT Additional search fees issued in connection with corresponding PCT Application No. PCT/US2015/060284 dated Feb. 9, 2016.
"Auisition / US Surgical Acquires sonopsy manufacturer NeoVision for $40mm", Pharma Intelligence, https://www.pharmamedtechbi.com/deals/199710172, pp. 1-4, Mar. 21, 2016.
"Tyco Acquires US Surgical for $3.3bn in a stock swap", Pharma Intelligence, https://www.pharmamedtechbi.com/deals/199810055, pp. 1-4, Mar. 21, 2016.
Saunders, Robert S., Jr., et al.; "The Effect of Breast Compression on Mass Conspicuity in Digital Mammography", American Association Physics Medicine, vol. No. 35, Issue No. 10, pp. 4464-4473, Oct. 2008.
U.S. Non-Final Office Action issued in connection with Related U.S. Appl. No. 14/572,452, dated Nov. 1, 2016.
U.S. Final Office Action issued in connection with Related U.S. Appl. No. 14/572,452, dated Mar. 21, 2017.

\* cited by examiner

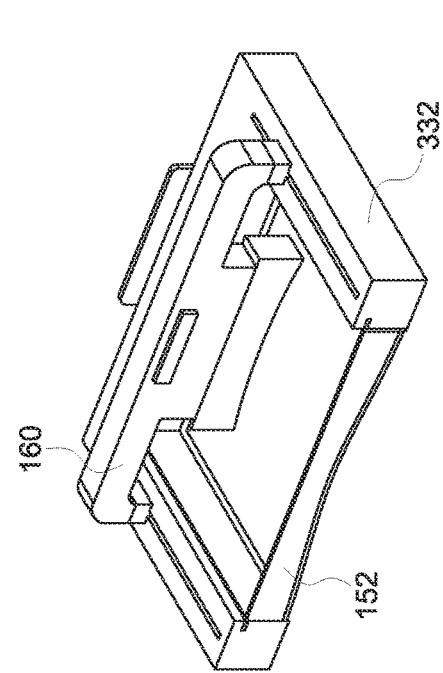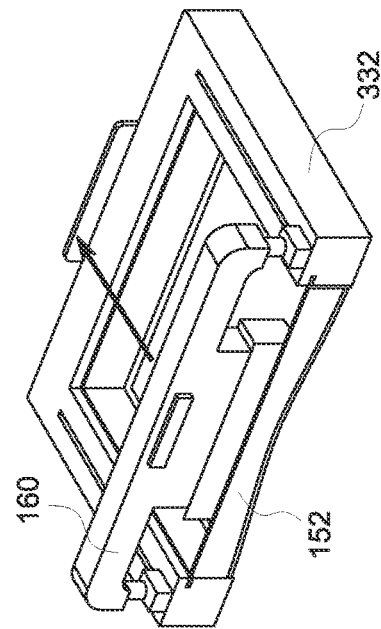
FIG. 13

BREAST IMAGING METHOD AND SYSTEM

BACKGROUND

The present approach relates generally to the field of breast cancer screening and, more specifically, to the use of tomosynthesis and ultrasound imaging for acquiring breast images.

In modern healthcare facilities, non-invasive imaging approaches are used for identifying, diagnosing, and treating diseases. One purpose to which such techniques are applied is the acquisition of breast images for use in identifying and diagnosing lesions or irregularities in the breast tissue.

In conventional mammography approaches, breast imaging may be implemented using radiographic techniques, such as by projecting X-rays through the breast tissue and reconstructing images based on the differential transmission of the X-rays through the tissue. Such approaches, however, may suffer from various detriments. For example, conventional radiographic imaging techniques are generally planar or two-dimensional in nature, limiting the ability of a diagnostician to visualize the results.

An alternative approach to conventional radiographic mammography involves an imaging technique known as tomosynthesis. In tomosynthesis X-ray attenuation data is obtained for a region of interest over an angular range (e.g., 30°, 45°, 90°, and so forth) and this data is used to construct volumetric or generally three-dimensional reconstruction of the breast tissue. In general, tomosynthesis imaging exhibits good in-plane resolution with, potentially, poorer depth resolution. In this manner, tomosynthesis may be employed to non-invasively detect abnormalities in the breast tissue, such as lumps, fibroids, lesions, calcifications, and so forth. Such tomosynthesis systems are generally effective for detailed characterization of benign and cancerous structures such as calcifications and masses embedded in the breast tissue.

Another imaging approach for use in imaging breast tissue is ultrasound. An ultrasound imaging system uses an ultrasound probe for transmitting ultrasound signals into an object, such as the breast of the patient being imaged, and for receiving reflected ultrasound signals there from. The reflected ultrasound signals received by the ultrasound probe are generally indicative of boundary transition between structures in the imaged region and may be used to reconstruct an image of the interior of the tissue. In general, ultrasound may exhibit good depth-resolution combined with a somewhat reduced in-plane resolution. Ultrasound imaging is useful as an alternate tool for diagnosis, such as for differentiating benign cysts and masses. In addition, ultrasound imaging may be used as a secondary screening tool in women with breasts that are dense. In dense breast tissue X-ray imaging is not as sensitive and the addition of ultrasound imaging has been shown to find more cancers.

In practice, it may be desirable to utilize multiple imaging approaches when evaluating a patient, such as by acquiring both tomosynthesis and ultrasound imaging data. To be able to relate the respective data sets, it may be desirable to acquire the image data at roughly the same time and with the patient in the same position for both data acquisitions. Hence it may be desirable to utilize a combined tomosynthesis and ultrasound imaging system that allows rapid and sequential acquisition of the respective image data sets. However, one impediment to the design and use of such systems in this manner is the interference that the various parts of one systems may have on the other system, such as the presence of an ultrasound probe in the vicinity of the X-ray beam path, and the need to minimize or coordinate the operations to be performed by the attending technologist.

BRIEF DESCRIPTION

In one embodiment, a breast imaging system is provided. The breast imaging system includes: a frame structure comprising an open region; an ultrasound probe attached to the frame structure and configured to move along the frame structure over the open region during operation; and one or more pivot structures about which the frame structure is configured to pivot with respect to a compression paddle.

In a further embodiment, a breast imaging system is provided. The breast imaging system includes: a frame structure comprising an open region and one or more engagement structures. The breast imaging system also includes: a removable ultrasound probe comprising one or more complementary structures configured to engage and disengage the engagement structures, wherein the ultrasound probe is configured to move along the frame structure over the open region during operation.

In an additional embodiment, a method for acquiring breast data is provided. In accordance with this method, breast tissue is pulled into the field of view and maintained in this positioning with a mild compression to a non-uniform thickness. One or more tomosynthesis images are acquired of the breast tissue. An ultrasound probe is positioned on the breast tissue. In certain embodiments, the ultrasound probe is at least 15 cm long (such as 19 cm to 30 cm long) so as to span the entire breast tissue in one pass of the probe. In addition, as discussed herein, the ultrasound probe may be configured for a fast readout, such that the ultrasound sweep or scan can be performed in a minute or less. In addition, in certain embodiments, the ultrasound probe may have surfaces curved to match the shape of the breast in cranio-caudal (CC) views and/or flat or only partially curved to match the breast shape in mediolateral-oblique (MLO) views. In one implementation, the ultrasound probe is positioned outside the X-ray beam path during acquisition of the one or more tomosynthesis images and within the X-ray beam path when positioned on the breast tissue. The ultrasound probe is moved along a defined scan path. One or more ultrasound images are acquired of the breast tissue using the ultrasound probe. Compression of the breast tissue is released.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present approach is directed towards acquisition of breast image data, such as the acquisition of ultrasound breast image data. For example, in certain embodiments, an automated ultrasound scanning system is described which may be used to implement a pre-programmed scan protocol in an automated manner. Such scans may be performed by moving an ultrasound probe across the breast tissue of a patient without user intervention or guidance during the scan operation.

In certain embodiments discussed herein, the ultrasound scan probe and support mechanism are configured to be used in a multi-modality mammography imaging system, such as a combined tomosynthesis and ultrasound imaging system. For example, in such an embodiment, the ultrasound components may be positioned and configured so as not to interfere with the tomosynthesis imaging operation, such as to remain out of the X-ray beam path. Further, the ultrasound probe and associated components may be configured to as to move and scan the breast tissue under compression, such as under the compression provided by one or more paddles used in the tomosynthesis imaging operation, so that the acquired image data may be more easily associated due to the conformity of the tissue between the two separate imaging operations. Thus, in such combined embodiments, the tomosynthesis and ultrasound image data may be obtained sequentially (or otherwise close in time) in one patient setting after the patient has been prepared, without having to move or reposition the patient.

Though certain of the present embodiments discussed herein are provided in the context of a combined imaging system (such as a combined ultrasound and tomosynthesis imaging system) it should be appreciated that such examples are provided for illustration and explanation only and are not intended to be limiting. In particular, certain aspects of the present ultrasound imaging approach may be implemented in imaging contexts that only involve the acquisition of ultrasound image data or, in other contexts, involve the acquisition of ultrasound image data in conjunction with other types of image data than those discussed herein (e.g., tomosynthesis image data). Thus, it should be understood and appreciated that the present examples are selected and presented so as to facilitate explanation of the present approach, but are not intended to be exhaustive or limiting as to the scope of possible implementations.

Figure 1:
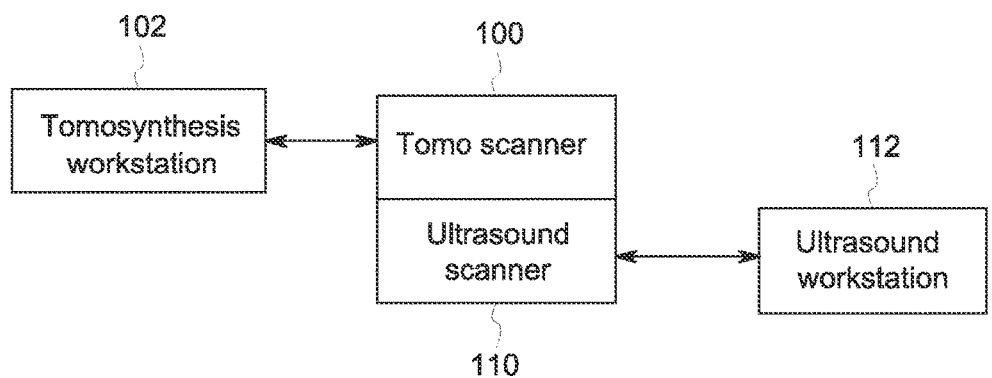
FIG. 1 is a block diagram of a combined tomosynthesis and ultrasound breast system, in accordance with aspects of the present disclosure.

With this in mind and turning to FIG. 1, a simplified system figure is depicted providing a high level view of certain components and aspects of one example of a multi-modality imaging system is provided. In this example, a tomosynthesis scanner 100 is provided in conjunction with a tomosynthesis workstation 102 that controls operation of the scanner 100. For example, a user may configure or initiate a tomosynthesis scan using the scanner 100 via the workstation 102 or may review tomosynthesis images generated during a scan session using the scanner 100.

In the depicted example, the tomosynthesis scanner 100 is provided in proximity to an ultrasound scanner 110, which may have a probe or other scan components which can be used to ultrasonically scan the patient during the same session, such as before or after the tomosynthesis acquisition. For example, the ultrasound image acquisition may be performed immediately after the tomosynthesis image acquisition, while the patient is still in the same position and, in the case of mammography, under compression. As with the tomosynthesis scanner 100, the ultrasound scan components 110 are shown as being in communication with an ultrasound workstation 112, which may be used to configure or program an ultrasound acquisition using the scanner 110 or to view the results of such a scan.

In one example, a motion controller/automation module is provided as part of the ultrasound workstation 112, the ultrasound scanner 110, or as module having components on both the workstation 112 and scanner 110, such as to communicate between the components and coordinate motion of the scanner 110. For example, in certain embodiments, the module is configured to automatically move the ultrasound probe of the scanner 110 to perform an ultrasound acquisition. In some such embodiments, a user may configure the scan via the workstation 112 and, based upon the configured scan, the motion controller/automation module may move the ultrasound scan components so as to acquire ultrasound images corresponding to the requested scan. Thus, the motion controller/automation module, as discussed in greater detail herein, may cause the movement of the ultrasound probe or other ultrasound imaging components over the target tissue so as to acquire the ultrasound image data corresponding to the prescribed scan.

Figure 2:
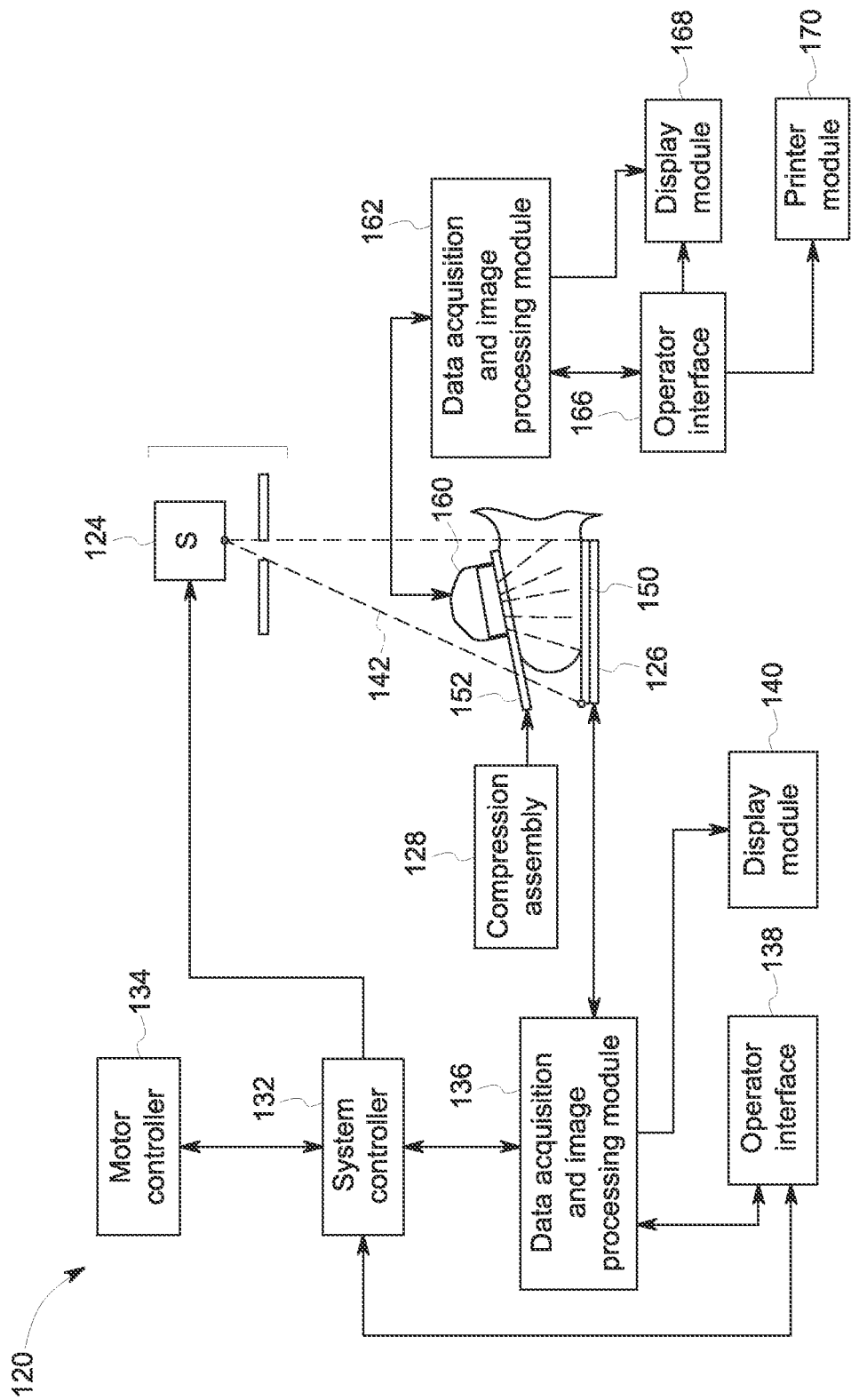
FIG. 2 is a diagrammatic representation of one embodiment of a multi-modality mammography imaging system in accordance with aspects of the present disclosure.

Turning to FIG. 2, an example of a combined, multi-modality imaging system 120 (including both tomosynthesis and ultrasound components) for use in accordance with the present approach is illustrated diagrammatically. As depicted, the imaging system 120 includes a tomosynthesis image data acquisition subsystem for acquiring tomographic image data. The tomosynthesis imaging subsystem includes an X-ray source 124, an X-ray detector 126 and a compression assembly 128 that may be used to position the patient tissue and to generate signals representative of X-ray transmission through the tissue of interest. The tomosynthesis imaging subsystem further includes a system controller 132, a motor controller 134, data acquisition and image-processing module 136, an operator interface 138 and a display module 140, some or all of which may be embodied as the tomosynthesis workstation 102.

The X-ray source 124 may, in certain implementations, include an X-ray tube (or other suitable X-ray generating mechanism) and a collimator configured to generate a beam of X-rays 142 when active. In an implementation of a tomosynthesis imaging system, the X-ray source 124 is movable in a one, two or three dimensional trajectory relative to the volume being imaged (such as along a line or a curve) such that the X-ray source moves over a limited angular range relative to the volume being imaged. Movement of the X-ray source may be manual, automated, or some combination (e.g., manual initial positioning with automated movement during scanning).

In certain embodiments, an X-ray filtration slot may be provided on the outside of the X-ray tube assembly. When the mesh paddle is used, as discussed herein, added filtration may thereby be provided to absorb low energy X-rays normally absorbed by the plastic compression paddle. These X-rays, if not absorbed, do not penetrate the breast and, thus, do not contribute to imaging, and only serve as added skin dose. Alternatively, this added filtration can be automatically inserted and internal to the X-ray tube system for when the mesh paddle is inserted.

The X-ray detector 126 may be stationary, or may be configured to move either independently or in synchrony with the X-ray source 124. In a mammography embodiment, the X-ray detector 126 may be positioned proximate to and beneath the breast tissue of the patient, and thus may be incorporated as part of or proximate to the compression assembly 128. For example, the X-ray detector 126 may be disposed immediately or proximately beneath a bottom plate of compression assembly 128 such that the breast tissue does not rest directly on the detector 126 but on a plate or other compression support above the detector 126. In addition, an anti-scatter grid may be placed between the detector and the compression support. This anti-scatter grid may be stationary or may move reduce the effects of the form (lines) of the grid from appearing in the image.

In certain breast imaging embodiments, the compression assembly 128 is configured to compress the breast tissue during both tomosynthesis and ultrasound image acquisitions. In particular, the compression assembly 128 may be used to stabilize the imaged breast tissue during acquisition of both the tomosynthesis and the ultrasound datasets and to maintain uniformity of the tissue both during and between image acquisitions. Thus, in practice, at least part of the compression structures of the assembly 128 may transmit X-rays (i.e., may be radiolucent) for the tomosynthesis image acquisition) and may transmit the ultrasound signals (i.e., may be sonolucent) for the ultrasound image acquisition. In one embodiment, the compression assembly includes a lower plate 150, (such as a flat, inflexible plate) on which the breast tissue may rest, and an upper plate or paddle 152 which lowers onto the breast tissue to effect compression. In one implementation, the upper paddle 152 is non-rigid across at least a portion of its surface. For example, the upper paddle 152 may be formed using a mesh material (i.e., formed as a mesh paddle) that is both radiolucent and sonolucent and which is at least partially conformable to the shape and size of the breast tissue. Conversely, in certain embodiments, the bottom paddle (i.e., lower plate 150) is only radiolucent, not sonolucent.

In a tomosynthesis implementation, and unlike conventional radiographic mammography techniques, it is not necessary for the breast tissue to be compressed to a substantially uniform thickness or to significantly reduce thickness. Furthermore, as the overlapping tissue structures in 2D imaging can be resolved with tomosynthesis the breast tissue does not require compression in order to spread out the tissue. That is, due to the nature of the tomosynthesis image acquisition process, the breast tissue need not be thin and of uniform thickness in order to generate useful diagnostic images. Likewise, the ultrasound image acquisition does not require that the breast tissue be of uniform thickness. Thus, in certain embodiments the upper plate 152 may rotate or approach the lower plate 150 at an angle such that, when engaged, the paddles or plates 150, 152 are not parallel to one another but, instead, remain at an angle with respect to one another. Such accommodative compression may reduce patient discomfort by at least partly conforming to the shape of the breast tissue.

In the depicted implementation, the system controller 132 controls operation of the tomosynthesis imaging subsystem and provides for any physical motion of the X-ray source 124 and/or the X-ray detector 126. In the depicted embodiment, mechanical movement of the imaging components is effected via the motor controller 134 in accordance with a prescribed imaging trajectory for use in tomosynthesis. Therefore, by means of the tomosynthesis imaging subsystem, the system controller 132 may facilitate acquisition of radiographic projections at various views along a limited angular range relative to a patient. In general, the system controller 132 commands operation of the tomosynthesis imaging system 120 to execute examination protocols and to acquire resulting data.

In one implementation, the tomosynthesis data acquisition and image-processing module 136 communicates with the X-ray detector 126 and typically receives data from the X-ray detector 126, such as a plurality of sampled analog signals or digitized signals resulting from exposure of the X-ray detector to X-rays. The tomosynthesis data acquisition and image-processing module 136 may convert the data to digital signals suitable for processing and/or may process sampled digital and/or analog signals to generate volumetric images of the breast tissue which may, in turn, be displayed on the display module 140.

The operator interface 138 can be used to customize settings for the tomosynthesis imaging and for effecting system level configuration changes as well as for allowing operator activation and operation of the tomosynthesis imaging system 120. In the depicted embodiment, the operator interface 138 is connected to the system controller 132, image-processing module 136, and the display module 140.

Shown in conjunction with the tomosynthesis imaging subsystem components discussed above are ultrasound imaging system components that may be present in a combined (i.e., multi-modality) system. In the depicted example, the ultrasound imaging subsystem includes an ultrasound probe 160, an ultrasound data acquisition and image-processing module 162, which includes beam-formers and image reconstruction and processing circuitry, an operator interface 166, a display module 168 and a printer module 170. In a multi-modality imaging system based upon both X-ray and ultrasound techniques, certain of these components or modules may be partially or fully integrated to perform image acquisition and processing for both systems. Alternatively, in other implementations, both the X-ray and ultrasound subsystems may be largely autonomous from one another, with separate user workstations or interfaces as well as separate scan subsystems.

In certain embodiments, the ultrasound imaging subsystem uses the ultrasound probe 160 for transmitting a plurality of ultrasound signals into an object, such as the breast tissue of a patient being imaged, and for receiving a plurality of reflected ultrasound signals from the tissue. In certain implementations, the ultrasound imaging subsystem may employ beam steering techniques to help image all areas of the breast tissue. The reflected ultrasound signals from the tissue convey information about thickness, size, and location of various tissues, organs, tumors, and anatomical structures in relation to transmitted ultrasound signals. The plurality of reflected ultrasound signals received by the ultrasound probe 160 are processed for constructing an image of the object.

In certain embodiments, the ultrasound probe is at least 15 cm long (such as 19 cm to 30 cm long) so as to span the entire breast tissue in one pass of the probe. In addition, as discussed herein, the ultrasound probe may be configured for a fast readout, such that the ultrasound sweep or scan can be performed in a minute or less. In addition, in certain embodiments, the ultrasound probe may have surfaces curved to match the shape of the breast in cranio-caudal (CC) views and/or flat or only partially curved to match the breast shape in mediolateral-oblique (MLO) views.

In certain embodiments, movement and operation of the ultrasound probe 160 is automated, as will be discussed in greater detail below. In these embodiments, the ultrasound probe 160 may be automatically brought into contact with the tissue being imaged or with the overlying sonolucent paddle structure 152 compressing the breast tissue. The ultrasound probe 160 may then be moved via a mechanical subsystem (e.g., motion controller/automation module) with respect to the breast tissue while acquiring ultrasound image data. In some embodiments, upon completion of the prescribed acquisition protocol, one or both of the ultrasound probe 160 or the underlying paddle 152 may be automatically disengaged from the tissue. In certain implementations, the ultrasound probe 160, and any radiopaque supporting structures, are removed from the X-ray beam path when a tomosynthesis examination is being performed or, more generally, when an ultrasound examination is not being performed.

The ultrasound data acquisition and image-processing module 162 sends signals to and receives information from the ultrasound probe 160 during an imaging procedure. Thus, the ultrasound data acquisition and image-processing module 162 may control the strength, beam focus or forming, duration, phase, and frequency of the ultrasound signals transmitted by the ultrasound probe 160, and may decode the information contained in the plurality of reflected ultrasound signals from the tissue to a plurality of discernable electrical and electronic signals. Once the information is obtained, an ultrasound image of the object located within a region of interest is reconstructed in accordance with generally known reconstruction techniques.

The operator interface 166 may include a keyboard, a mouse, and other user interaction devices. The operator interface 166 can be used to customize a plurality of settings for an ultrasound examination (including settings related to the automated operation of the probe 160), to effect system level configuration changes, and to allow operator activation and operation of the ultrasound imaging system 32. The operator interface 166 is connected to the ultrasound data acquisition and image-processing module 162, the display module 168 and to the printer module 170, some or all of which may be provided as the ultrasound workstation 112 of FIG. 1. The display module 168 receives image information from the ultrasound data acquisition and image-processing module 162 and presents the image of the object within the region of interest of the ultrasound probe 160. The printer module 170 is used to produce a hard copy of the ultrasound image in either gray-scale or color. As noted above, some or all of these system components may be integrated with those of the tomosynthesis X-ray system described above.

Figure 3:
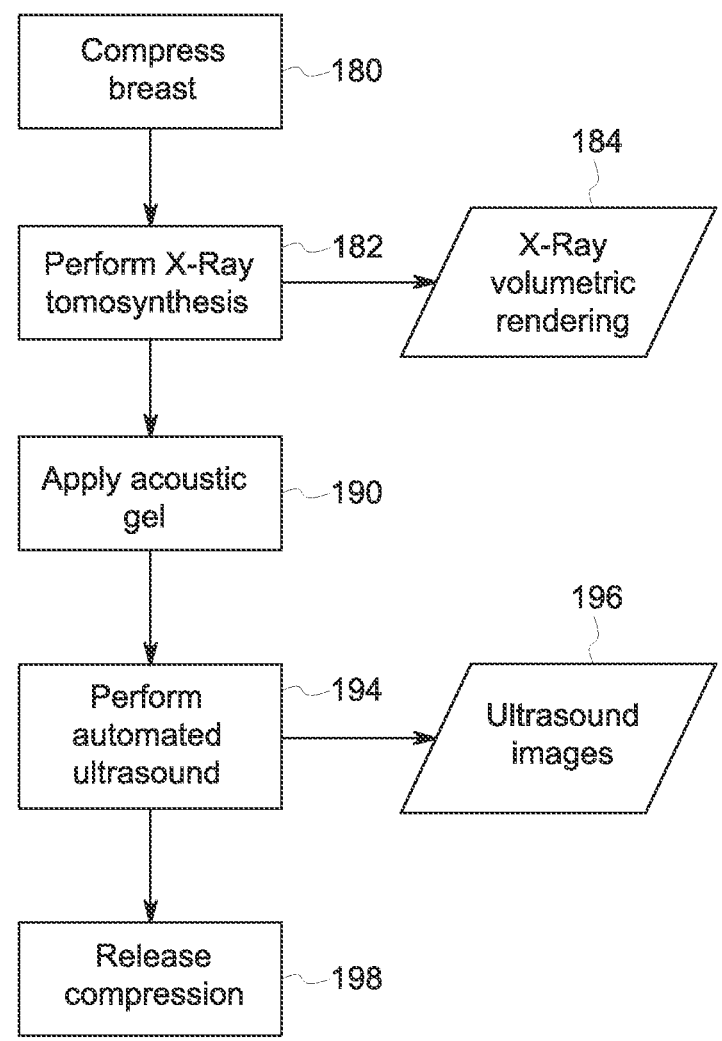
FIG. 3 is a process flow diagram of a combined tomosynthesis and ultrasound breast image acquisition, in accordance with aspects of the present disclosure.

Turning now to FIG. 3, an example of a process flow of one implementation of the present approach is illustrated in a flow chart. In this example, the breast tissue is initially compressed (block 180) to the desired thickness or range of thickness. As noted above, unlike conventional radiographic mammography approaches, the compression need not result in a uniform thickness of tissue being imaged and may instead be more accommodative of the breast shape by allowing a tapered or angled compression. In addition, the compression may be performed using a non-rigid paddle structure 152, such as a mesh paddle structure, that is accommodative or conformable to the breast tissue size and shape.

In certain embodiments, compression force feedback or other approaches may be used to determine when the motion of the compression paddle 152 is stopped, i.e., when sufficient contact is established. For example, in one embodiment, compression of the breast tissue is stopped based upon specified or derived threshold criterion. In some embodiments, the change in force per unit distance moved by the paddle may be measured and monitored and, based upon this measure a determination may be made as to when compression is to be stopped (i.e., when a threshold force per distance value is reached). For example, compression may continue in certain implementations to a certain specified force or to a threshold point where the increase in achieved compression is reduced or negligible in view of the additional applied force.

In certain embodiments, one or more sensors (such as strain sensors provided on the edge of the paddle 152) may be monitored for an indication that the desired force threshold is reached, stopping compression. In other embodiments, the electrical properties of a wire or wires woven through a mesh material of the paddle 152 may be monitored and used to determine the force per unit area or force per unit distance moved, which may then be compared to a threshold. More generally, any pressure or tension sensing approach may be used, including implementations that don't utilize measuring the electrical properties of conductive wire. Examples of other pressure or tension sensing approaches that may be employed include, but are not limited to, use of piezoelectric materials, capacitive sensors, or optical fibers.

In one embodiment, the respective threshold used to evaluate when compression is sufficient may be based on values queried from a look-up table or determined from on-the-fly calculations. For example, in a look-up table embodiment, a table of compression force and thickness curves may be accessible to the system (such as stored on the system or on an accessible network location). Different curves may be provided for different sizes and types of paddles 152, and/or for different patient variable such as age, body mass index, breast or cup size, breast density, and so forth. As will be appreciated, different, interchangeable paddles may also be provided based on these factors or on combinations of these factors. Based on these examination specific factors, the appropriate curves may be queried to provide the correct compression threshold values. In such embodiments, the force sensors may provide measures of the trajectory of the paddle 152 on the breast and consultation with the appropriate table or curves may be used to determine a threshold for establishing sufficiency of the compression. In certain embodiments, the system may reduce compression by some nominal amount once the compression threshold is reached (e.g., by 1 mm or less) to improve patient comfort and to allow for any overshoot by the compression mechanism. Further, in certain implementations, the amount of compression may be changed (i.e., lessened or increased) between image acquisitions by different modalities if the respective modalities do not require or benefit from the same degree of compression. For example, in a tomosynthesis and ultrasound sequential acquisition, the tomosynthesis images may be acquired at a first compression while the ultrasound images are acquired at a second, lesser, degree of compression. In addition to added comfort for the patient the reduced compression will allow for the mesh to become less taught on the breast. This increased flexibility of the mesh will allow for better contact of the ultrasound probe when mild pressure is applied with the probe.

In the depicted example, an X-ray tomosynthesis is performed (block 182) on the compressed breast tissue and a resulting volumetric rendering 184 is generated. In certain implementations, an acoustic coupling gel or lotion may be applied automatically or by the technologist (block 190) prior to ultrasound imaging. In embodiments employing a mesh compression paddle 152, the mesh structure allows passage of the acoustic gel or lotion to facilitate acoustic coupling of the probe 160 through the paddle 152 and with the breast tissue. In the depicted example, an automated ultrasound scan is performed (block 194) and ultrasound imaged 196 generated. Upon completion of the scan, compression may be released (block 198) or reduced.

Figure 4:
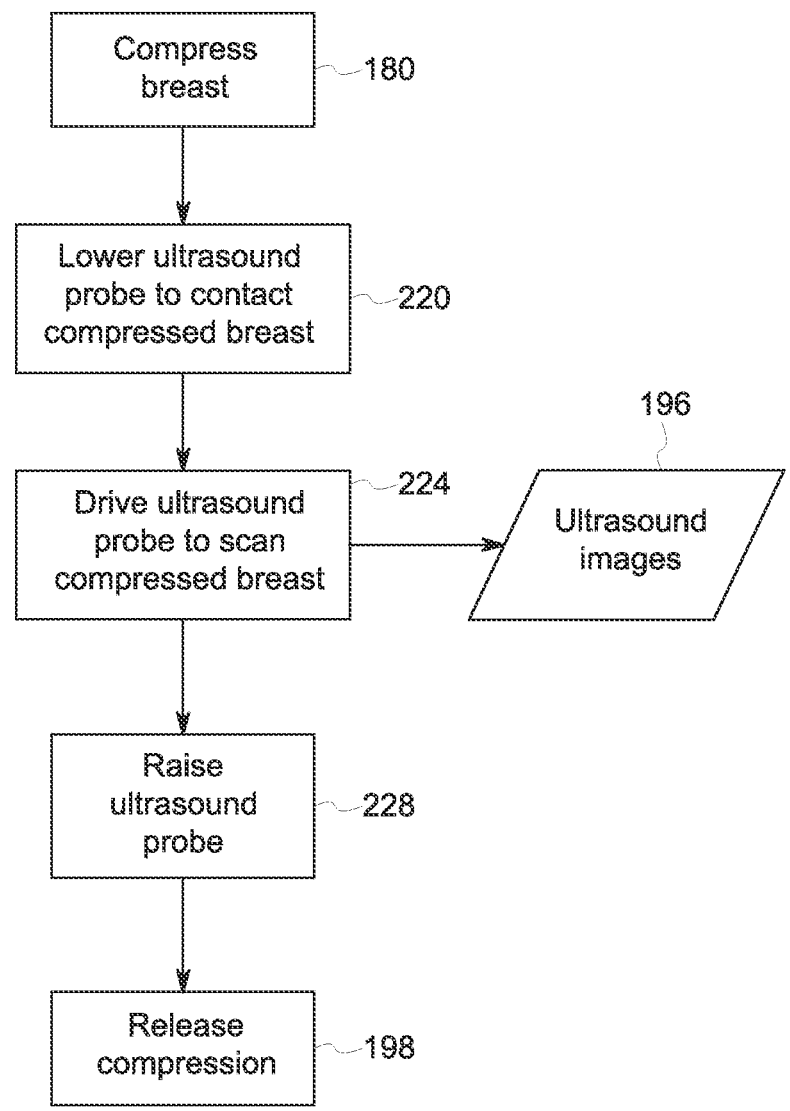
FIG. 4 is a process flow diagram of an ultrasound image acquisition in accordance with one embodiment of the present disclosure.

While FIG. 3 provides a generalized overview of a multi-modality imaging session, turning to FIG. 4, a process flow is provided describing aspects of an automated ultrasound image acquisition in greater detail. In this example, only the ultrasound imaging steps are depicted, though it should be understood that imaging steps for other imaging modalities, such as the tomosynthesis steps of FIG. 3, may also be performed in conjunction with the described ultrasound image acquisition.

Per the described implementation, upon commencing the ultrasound scan, an ultrasound probe 160 is automatically lowered (block 220) so as to contact the compressed breast tissue and/or the overlying paddle 152 structure (e.g., a sonolucent mesh paddle). For example, in one embodiment, the ultrasound probe 160 is flipped or otherwise moved from a first position (e.g., a vertical or non-ultrasound imaging position) to a second position (e.g., a horizontal or ultrasound imaging position).

Once positioned, the ultrasound probe 160 may be mechanically or electromechanically driven (block 224) along a defined path and may, while driven, acquire ultrasound image data of the underlying breast tissue. In certain embodiments, the probe 160 may be driven toward or away from the patient chest wall. Conversely, in other embodiments the probe 160 may be driven in a direction generally parallel to the chest wall (e.g., from left to right or vice versa with respect to the patient). From this acquired ultrasound image data one or more ultrasound images 196 may be generated. Upon completion of the defined movement across the breast tissue, the ultrasound probe 160 may be automatically raised (block 228) from contact with the breast tissue and/or the conformable paddle 152. For example, in one embodiment, the ultrasound probe 160 is flipped or otherwise moved from the second position (e.g., the horizontal or ultrasound imaging position) to the first position (e.g., the vertical or non-ultrasound imaging position).

Figure 5:
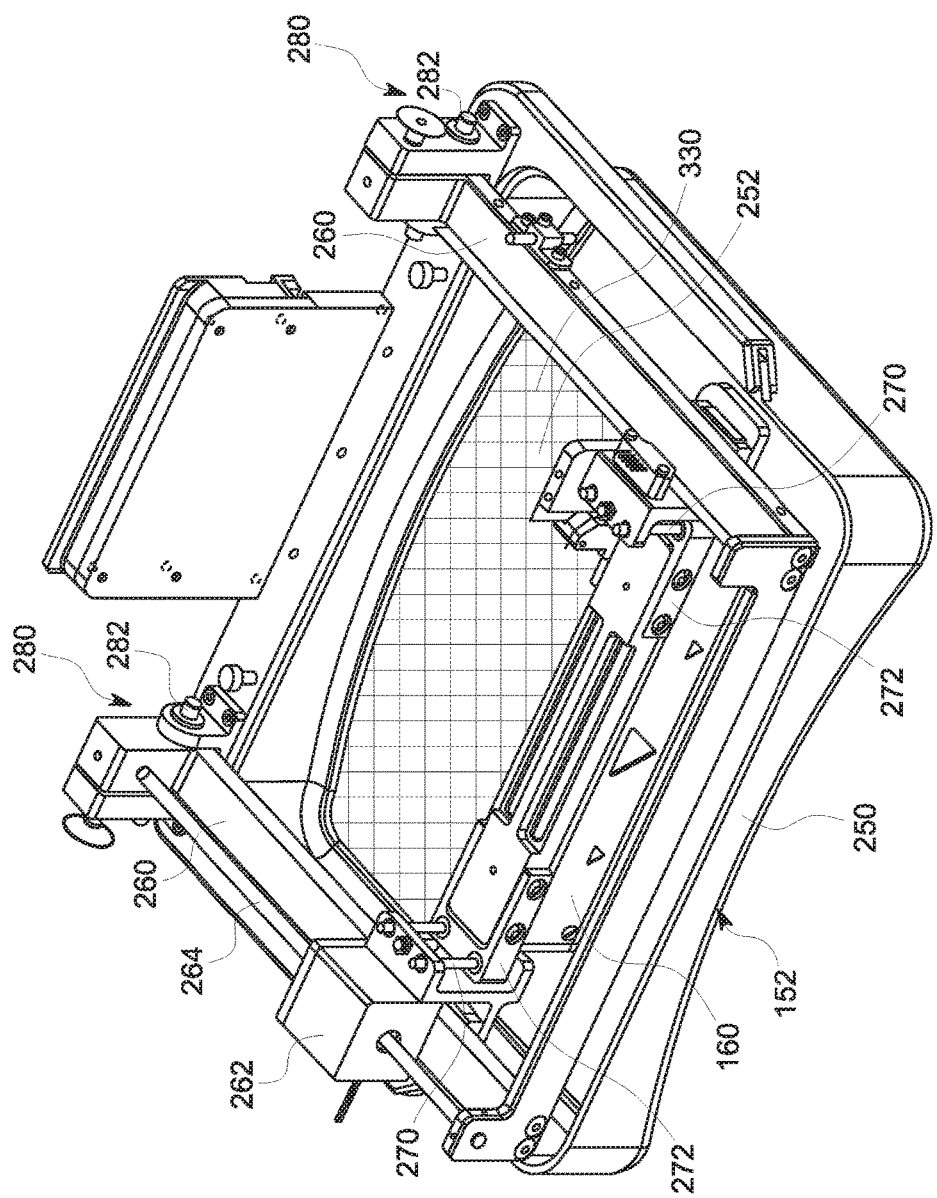
FIG. 5 depicts a perspective view of an ultrasound probe and associated support structure, in accordance with aspects of the present disclosure.

Turning to FIG. 5, an example of an ultrasound probe 160 and conformable paddle 152 is depicted which is suitable for use in an approach as outlined with respect to FIG. 4. In the depicted example, a paddle 152 is depicted which can apply a compression force to the breast tissue when engaged. The depicted example of a paddle 152 includes a frame 250 having a curved surface to accommodate the breast surface while still pulling the tissue from the body and applying compression to hold the tissue in the imaging field of view. The frame 250 may be formed from hard plastics or polymers (e.g., engineering plastic, stereolithography (SLA) resins such as Accura BlueStone, Acurra ClearVue, and other resins suitable for use in 3D printing or other fabrication systems), ceramics, composites, metal, or some combination of these materials. The curvature of the frame 250 may be uniform across the paddle 152 or may vary between the front and rear surfaces of the paddle 152, such as to accommodate different breast shapes and sizes. That is, different sizes, shapes, and curvatures of paddles 152 may be provided so as to accommodate patient variability.

In the depicted example, the frame 250 of the paddle 152 includes an open or cutout region 252 in which a mesh material 330, such as a polyester mesh material, may be secured. The mesh material 330, when so attached may be stretched or taut, may be relaxed or slack, or may be neither stretched or slack (i.e., have substantially zero tension). Thus, the paddle 152 formed from the frame 250 and a mesh material 330 may be formed and applied to patient so as to achieve the desired degree of compression of the breast tissue undergoing imaging. In certain embodiments, the paddle 152 may include a limited number of radio-opaque elements, such as thicker mesh elements at spaced intervals or interwoven radio-opaque wires, that may be discernible in tomosynthesis or X-ray images. Such elements may then be used in the respective image reconstruction process to provide information about the patient skin line, as well as the size, shape, curvature, and/or contour of the compressed breast tissue in the imaged volume.

In addition, FIG. 5 depicts the ultrasound probe 160 along with a fixed track 260 on which the ultrasound probe 160 may move back and forth. In the depicted example, the ultrasound probe 160 may move along the path defined by the tracks 260, such as due to the operation of a motor 262 (e.g., a stepper motor) attached to the ultrasound probe 160 and configured to move along a rail 264. As will be appreciated, other approaches for moving the probe 160 along the track 260 (or along a comparable defined path) including, but not limited to, a screw-based drive system or other drive system. Thus, in the depicted example the probe 160 may be characterized as being in a start or initial position and will move linearly toward the patient's chest wall during operation until the scan path is traversed and the scan completed, at which time the probe 160 may be moved back to the start position.

In addition, FIG. 5 also depicts a mounting structure for the probe 160 that allows for vertical motion of the probe 160 (relative to the horizontal plane defined by the tracks 260) during operation. In particular, in this example, vertical rails 270 are provided which allow the ultrasound probe 160 to move, via mounting structures 272, along the rails 270 as the probe 160 is moved along the scan path (i.e., along tracks 260). Thus, in such an embodiment, the ultrasound probe 160 may be actively (such as by mechanical or electromechanically application of force) or passively (such as by the use of springs or other bias members) biased downward toward the imaged tissue. The curvature or shape of the imaged tissue as well as the mesh material 330 affixed to the frame however, may act against this bias to move the ultrasound probe 160 along the rails 270, as needed, while still maintaining good acoustic contact between the probe 160 and the tissue.

Further, in the depicted example, the tracks 260, ultrasound probe 160, and rail 264 are mounted to a pivot or rotational mechanism 280 that, in this example, includes a pivot 282 about which the attached structures can pivot or rotate. In this manner, the tracks 260, probe 160, and related components may be rotated from an ultrasound imaging orientation (shown in FIG. 5) to a tomosynthesis (or other) imaging orientation in which the ultrasound components are out of the way with respect to the other imaging modality. While a pivot-type mechanism is shown in FIG. 5, in other embodiments other types of rotational or movement mechanisms may be employed so long as the ultrasound components may be moved from a first imaging configuration (e.g., an ultrasound imaging configuration) to a second imaging configuration (e.g., a non-ultrasound imaging configuration).

Figure 6:
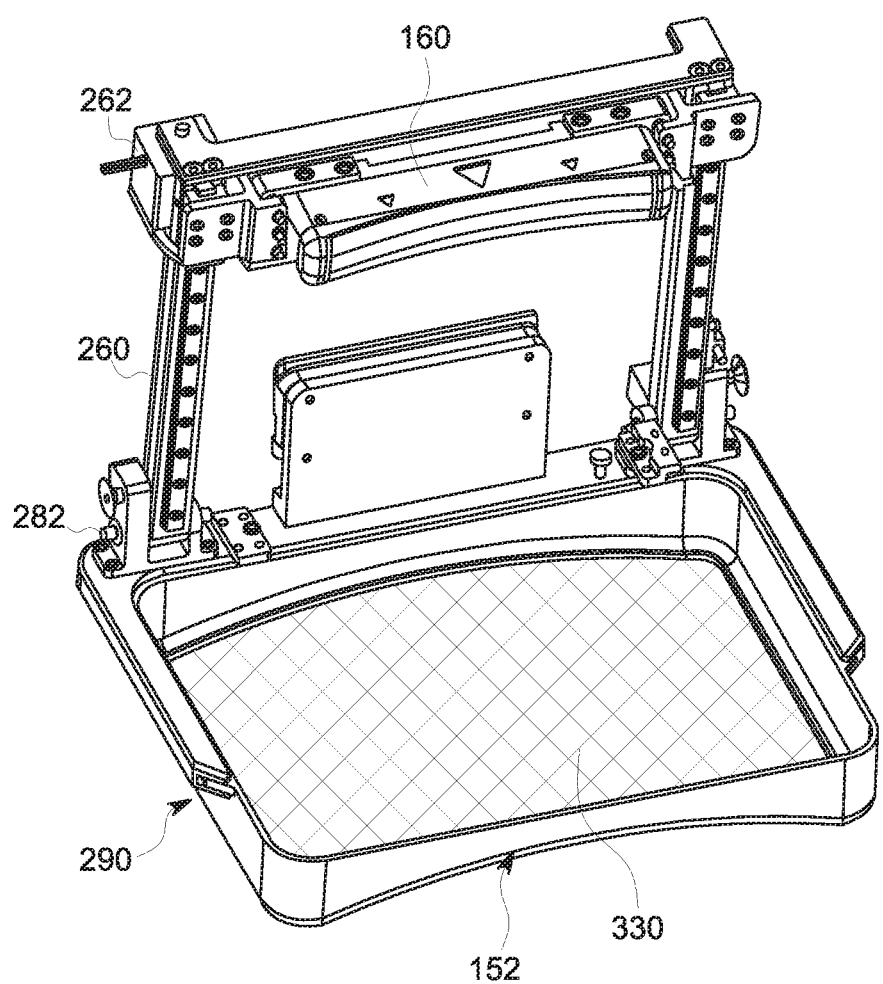
FIGS. 6-8 pictorially depict an example of an ultrasound scan approach, in accordance with aspects of the present disclosure.

With the preceding discussion in mind, FIG. 6 depicts the assembly of FIG. 5 in a "flip-up" configuration in which the ultrasound imaging components (e.g., probe 160, track 260) are rotated about the pivot 282 away from the paddle 152. In this example, the probe 160 is shown at an initial or start position for an ultrasound scan such that, when the assembly is lowered, the ultrasound scan will be ready to begin. In addition a sliding engagement 290 between the paddle 152 and the ultrasound component assembly is shown, illustrating the interchangeability of paddles 152 of different size, shape, composition, and so forth, as may be determined based on the patient characteristics. As can be seen in FIG. 6, both the patient-contacting surfaces of the paddle 152 and of the probe 160 may be curved so as to conform to the shape of the tissue surfaces to be imaged and the curvature of the ultrasound probe to enable better tissue contact with the ultrasound probe.

Figure 7:
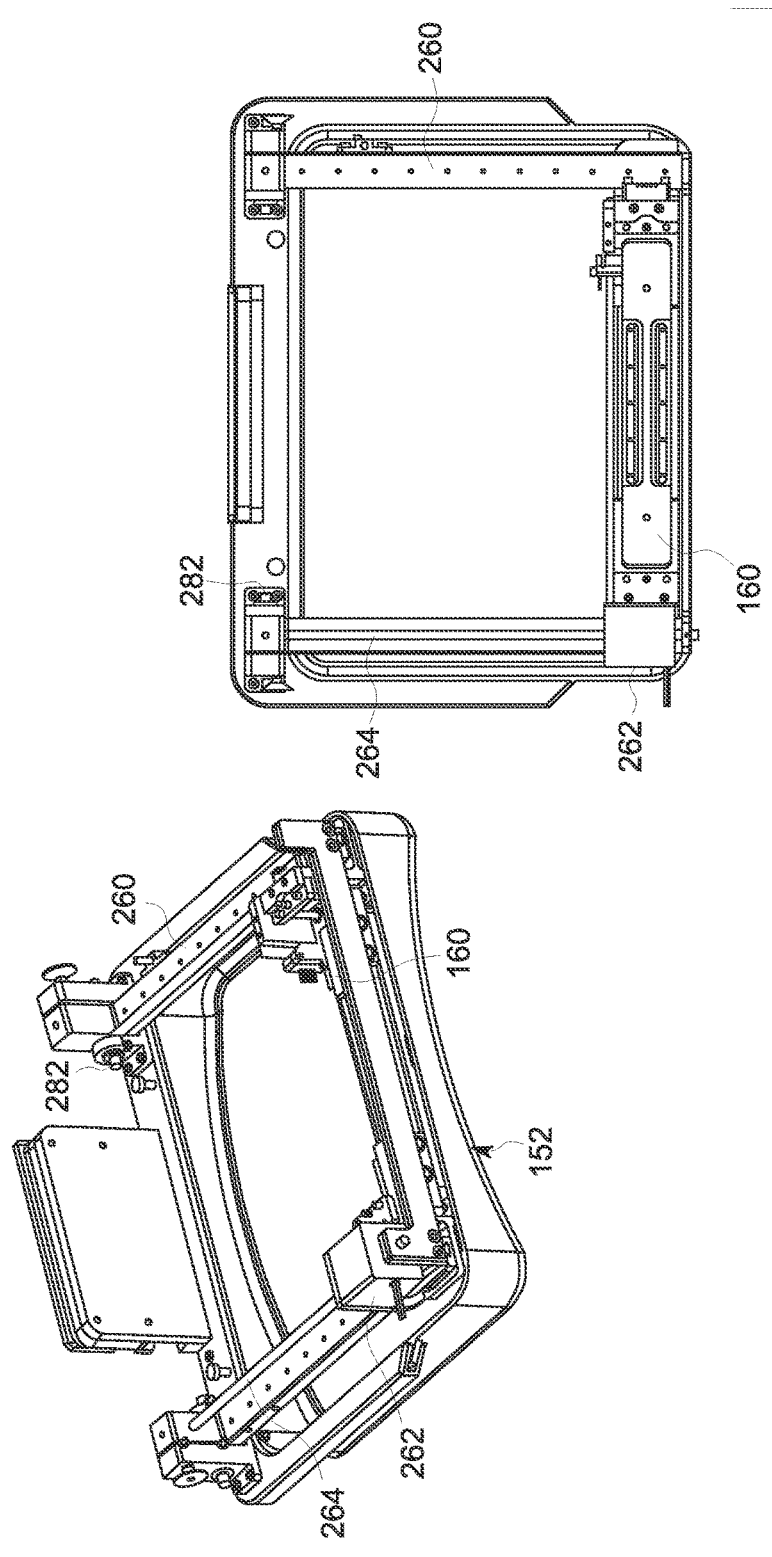
Figure 8:
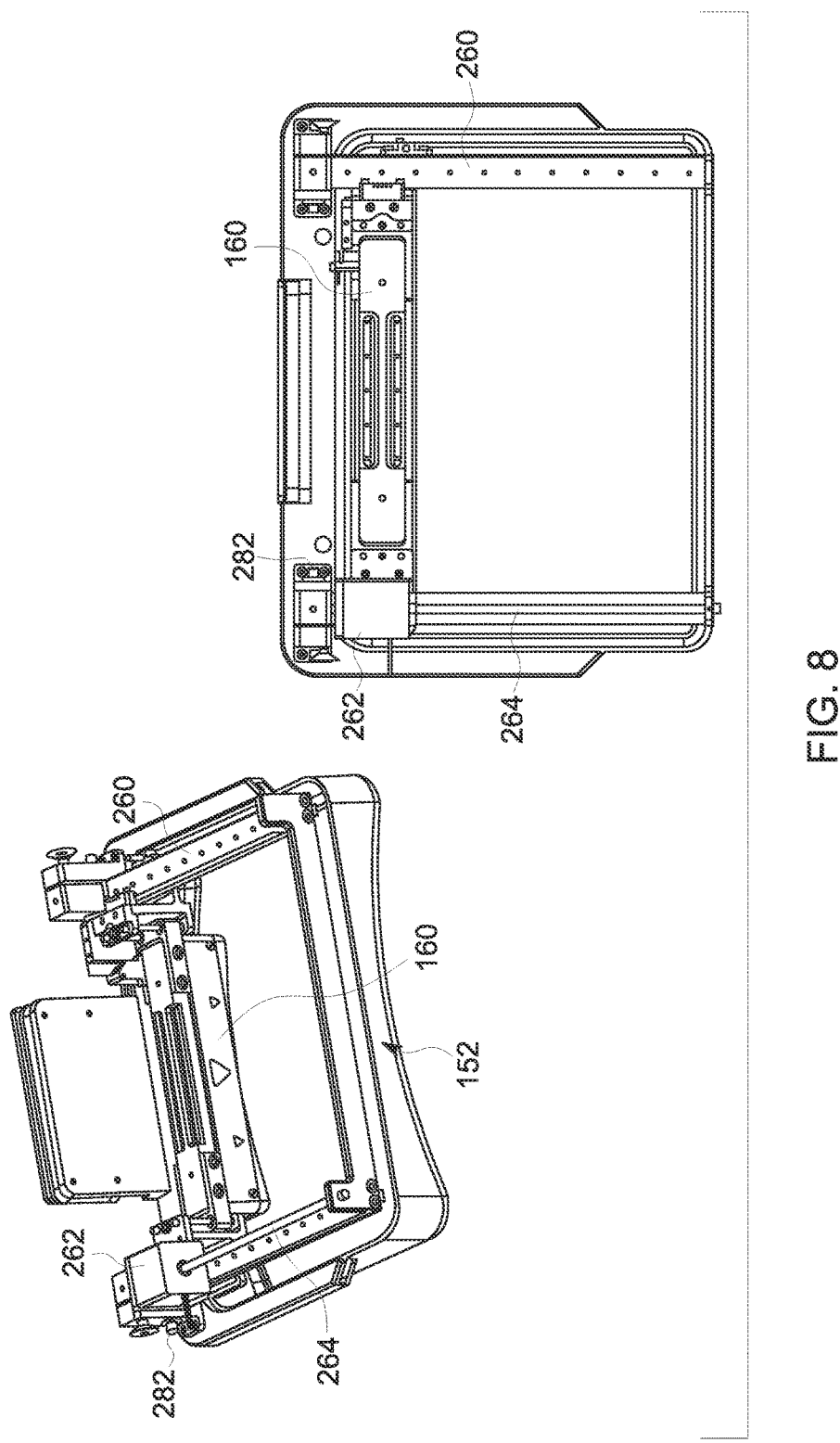

Turning to FIG. 7, a perspective (upper left) and top-down (lower right) view of the assembly of FIGS. 5 and 6 is shown after the probe 160 and associated ultrasound scan components have been rotated down about pivot 282 into an ultrasound scan position. In the depicted example, the scan has not begun and the probe head 160 is, therefore, still in the start position. Turning to FIG. 8, a perspective (upper left) and top-down (lower right) view of the assembly of FIGS. 5 and 6 is shown after completion of a scan, i.e., at the end position. As can be seen in this example, the motor 262 has moved along the rail 264 to move the probe head 160 down the tracks 260, thus conducting a scan pass of the underlying tissue.

Figure 9:
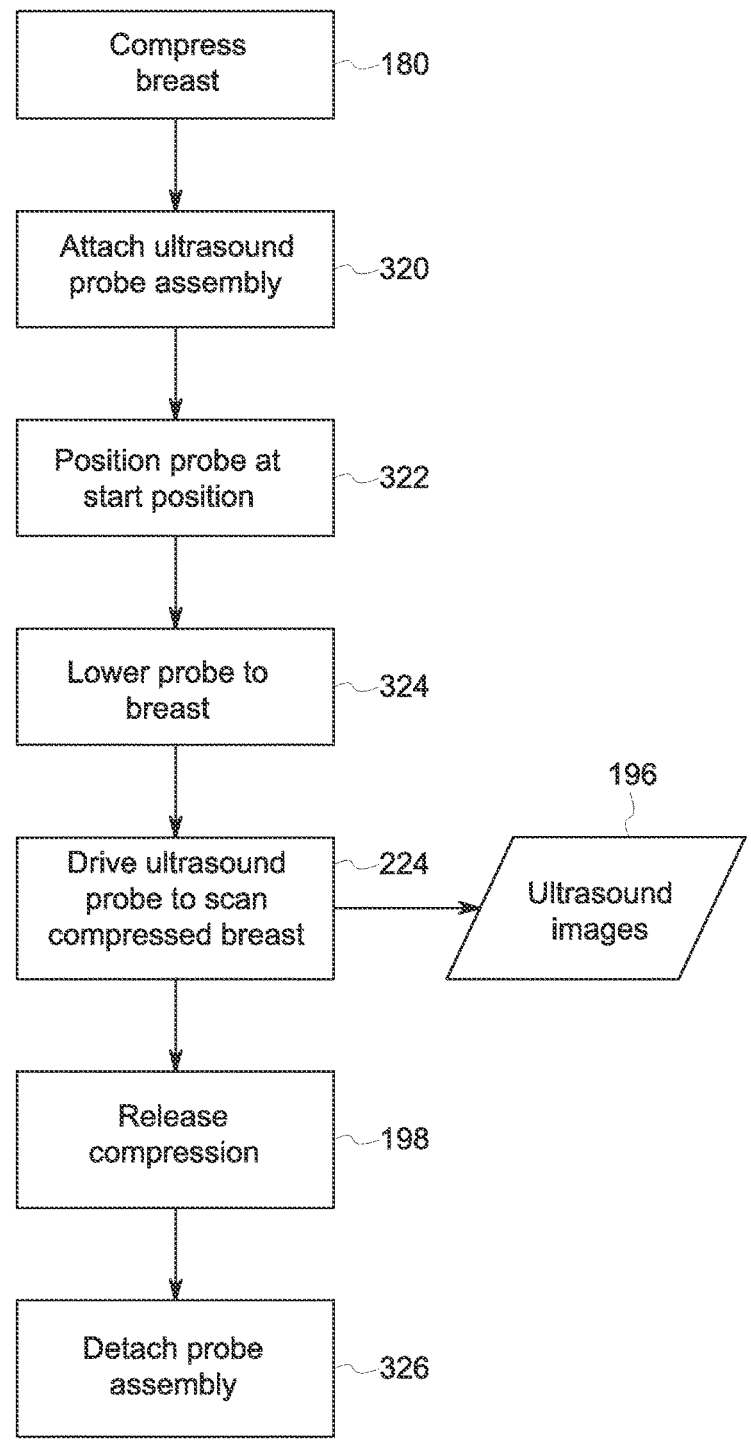
FIG. 9 is a process flow diagram of an ultrasound image acquisition in accordance with one embodiment of the present disclosure FIGS. 10-14 pictorially depict an example of an ultrasound scan approach, in accordance with further aspects of the present disclosure.

Turning to FIG. 9, another process flow is provided describing aspects of an additional automated ultrasound image acquisition in greater detail. In this example, the ultrasound imaging steps are depicted, though it should be understood that imaging steps for other imaging modalities, such as the tomosynthesis steps of FIG. 3, may also be performed in conjunction with the described ultrasound image acquisition.

In the depicted example, the breast tissue is compressed (block 180) as discussed herein, using a paddle assembly (such as a mesh paddle 152). As noted above, compression of the breast tissue for certain embodiments need not be uniform in implementations involving tomosynthesis and/or ultrasound imaging approaches. While the depicted example shows an order to the steps in which the probe 160 is attached and positioned subsequent to breast compression, it should be appreciated that in other implementations, the order of these steps may be reversed (i.e., breast compression may occur prior to attachment and positioning of the probe 160) or may be performed in parallel (i.e., generally concurrent with one another).

In the depicted example, an ultrasound probe 160 is attached (block 320) to a frame assembly and positioned (block 322) at a start position for conducting an ultrasound scan. The ultrasound probe 160 and associated frame or track may be attached or associated to the paddle assembly. A drive mechanism to drive the probe 160 along the frame may be built into the probe or may be provided as part of the frame assembly. In the depicted example, once the breast tissue is compressed and the probe 160 is attached and in a start position, the probe may be lowered (block 324) (e.g., mechanically or electromechanically) to be in contact (e.g., acoustic contact) with the breast tissue, either directly or through the mesh material of the paddle assembly 152.

Once the ultrasound probe 160 is in its start position and is lowered into contact with the breast tissue, the probe 160 may be mechanically or electromechanically driven (block 224) along a defined path and may, while driven, acquire ultrasound image data of the underlying breast tissue and position data (e.g., horizontal and vertical position data) of the probe. From this acquired ultrasound image data one or more ultrasound images 196 may be generated. The acquired probe position data may facilitate reconstruction of ultrasound images. Upon completion of the defined movement across the breast tissue, breast compression may be released (block 198) and the probe 160 may be detached (block 326) or otherwise removed from the assembly.

Figure 10:
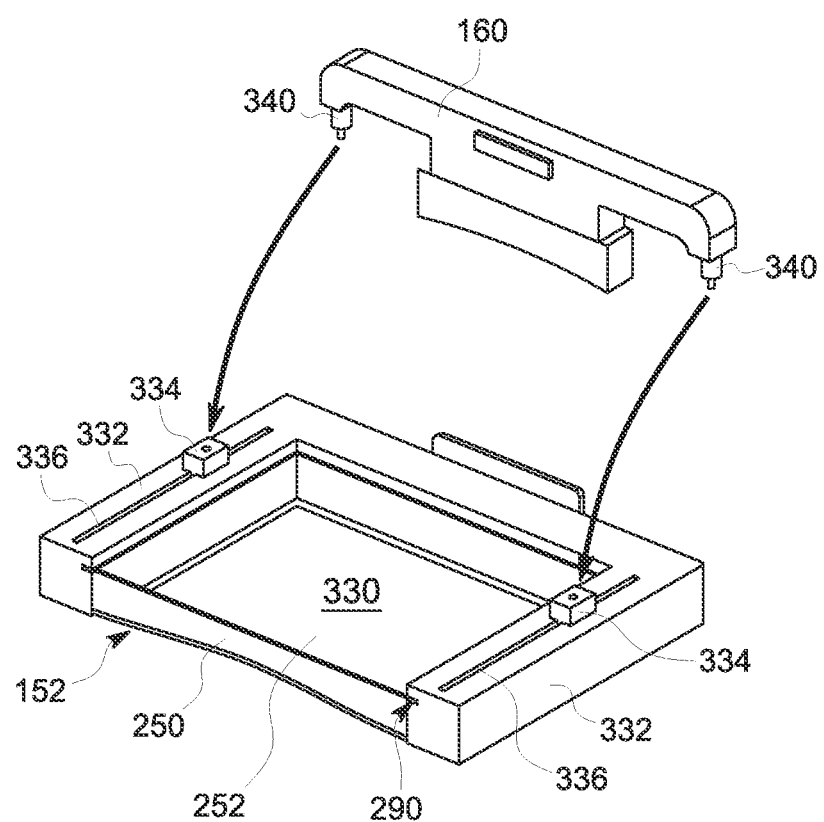

Turning to FIG. 10, an example of an ultrasound probe 160 and conformable paddle 152 is depicted which is suitable for use in the approaches outlined herein. In the depicted example, the paddle 152 includes a frame 250 having a curved surface to accommodate the breast surface while still applying compression. The frame 250, as noted above, may be formed from hard plastics or polymers (e.g., engineering plastic, SLA resins, or other compositions suitable for 3D printing or other fabrication approaches), composites, metal, or some combination of these materials. The curvature of the frame 250 may be uniform across the paddle 152 or may vary between the front and rear surfaces of the paddle 152, such as to accommodate different breast shapes and sizes. That is, different sizes, shapes, and curvatures of paddles 152 may be provided so as to accommodate patient variability and imaging techniques.

In the depicted example, the frame 250 of the paddle 152 includes an open or cutout region 252 in which a mesh material 330, such as a polyester mesh material, is secured. Thus, the paddle 152 formed from the frame 250 and a mesh material secured to the frame 250 (either at tension (i.e., taut) or with little or no tension (i.e., slack)) may be formed and applied to patient so as to achieve the desired degree of compression of the breast tissue undergoing imaging.

Figure 12:
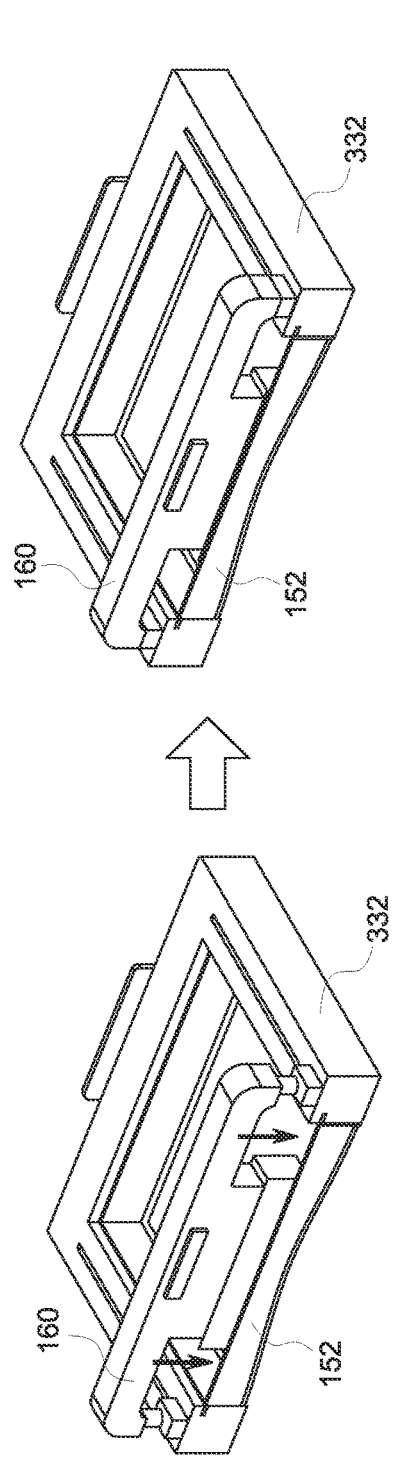

In addition, FIG. 10 depicts the ultrasound probe 160 as being separable from a frame 332 that defines a track on which the ultrasound probe 160 may move back and forth. That is, the ultrasound probe 160 may be attached to and removed from securement features 334 on the frame 332 that are configured to secure the probe 160 and move the probe 160, when attached, up and down relative to the frame 332 (as shown in FIG. 12), as well as along grooves, tracks, or slots 336 defined in the frame 332 In certain embodiments, the securement feature 334 on the frame 332 and the complementary features 340 on the probe 160 may be solely or combinations of mechanical, electrical or magnetic type features that allow an engagement and disengagement between the probe 160 and frame 332 to be easily formed. A stepping motor, screw-type drive, or other suitable motive mechanism may provide the force needed to drive the probe 160 along the frame 332 when engaged. This motive mechanism may be provided as part of the probe 160 or as part of the frame 332.

In the example, of FIG. 10, the probe assembly 160 is shown as detached from the frame 332. Directional arrows demonstrate the motion that may be employed to move the probe 160 toward the frame 332 and to secure the complementary feature 340 to the securement features 334.

Figure 11:
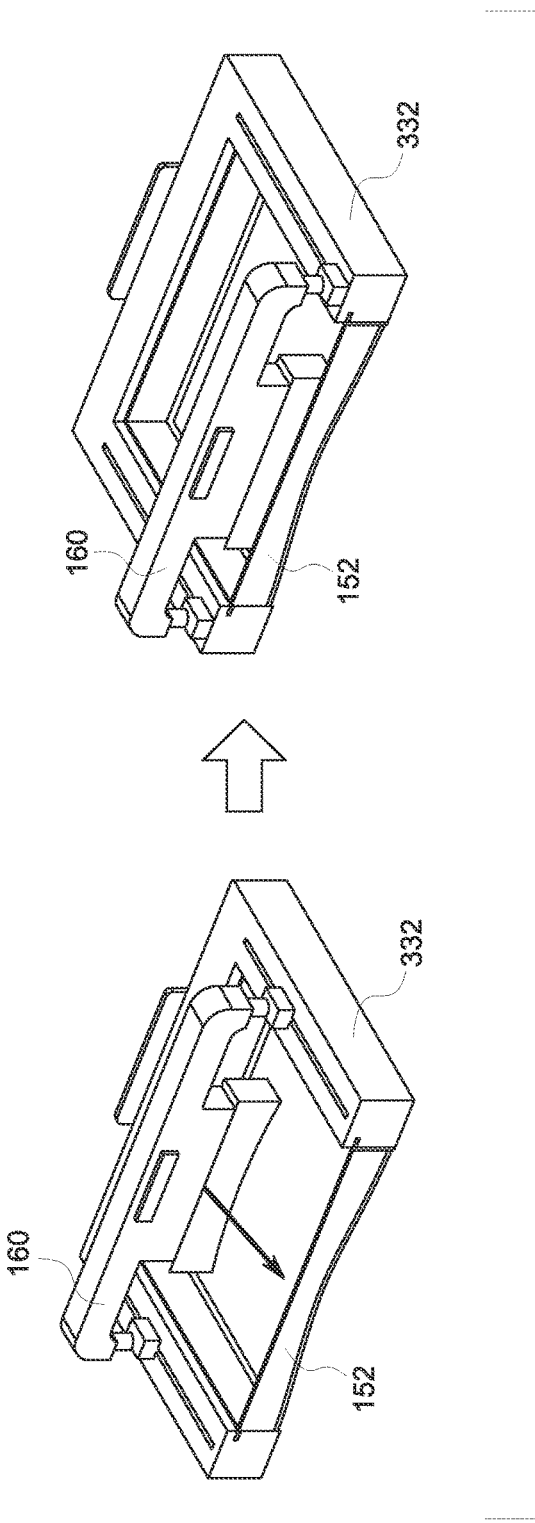

Turning to FIG. 11, once attached, the probe 160 may be driven or otherwise positioned at a start position (rightmost figure) on the frame 332, as shown in the sequence of figures and directional arrows of FIG. 11. Turning to FIG. 12, in embodiments where the probe is attached in a raised state or position relative to the breast tissue (i.e., elevated with respect to the frame 332), a step may be performed in which the probe 160 is lowered (relative to the frame 332) so as to come into acoustic contact with the tissue to be imaged. For instance, in the depicted example the engagement of the complementary features 340 and securement features 334 may allow for retraction of all or part of these features, such as into the frame 332 or into the securement features 334. In this manner, the probe 160 may be lowered relative to the frame 332 and brought into acoustic contact with the patient.

Once the breast tissue is compressed and the probe 160 is positioned and lowered, the probe 160 is driven (FIG. 13) from a start position (shown in the leftmost figure) to an end position (shown in the rightmost figure). As discussed herein, the probe 160 may be driven in an automated manner, such as using a motor mechanism under the control of a motion module of the ultrasound workstation. While driven, the ultrasound probe 160 may acquire ultrasound data in an automated fashion, which may in turn be used to generate ultrasound images 196. In addition, while driven, the probe 160 may acquire position data (e.g., horizontal and vertical position data for the probe) which may facilitate reconstruction of ultrasound images.

Figure 14:
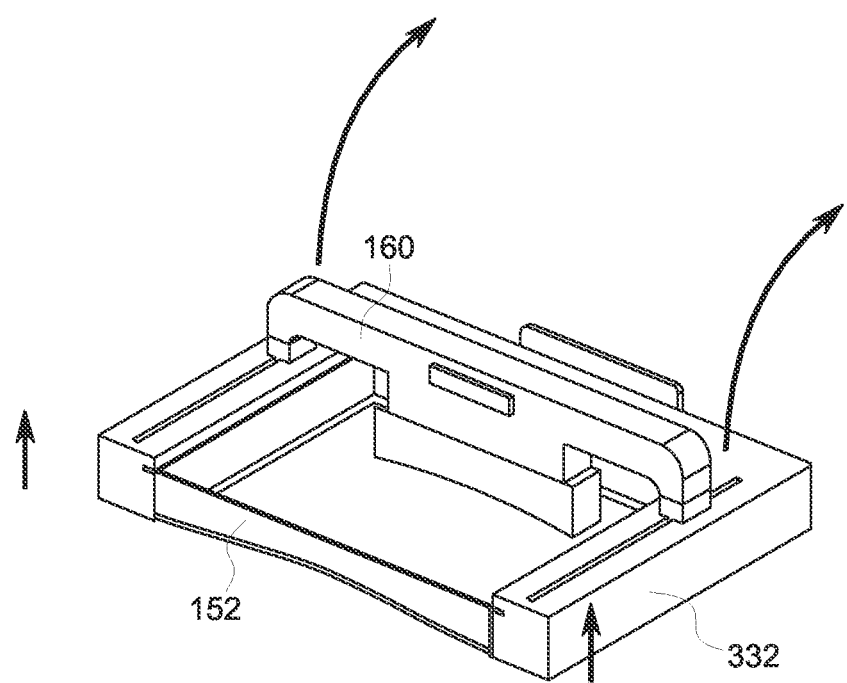

Turning to FIG. 14, after completion of the scan pass, the paddle 152 compression may be released or relaxed. In addition, the probe 160 may be detached from the frame 332, such as by release of the complementary feature 340 from the securement features 334. The ultrasound probe 160 may then be removed. As will be appreciated, when the probe 160 is detached, underlying breast tissue may be imaged using other imaging modalities, including tomosynthesis modalities.

Figure 15:
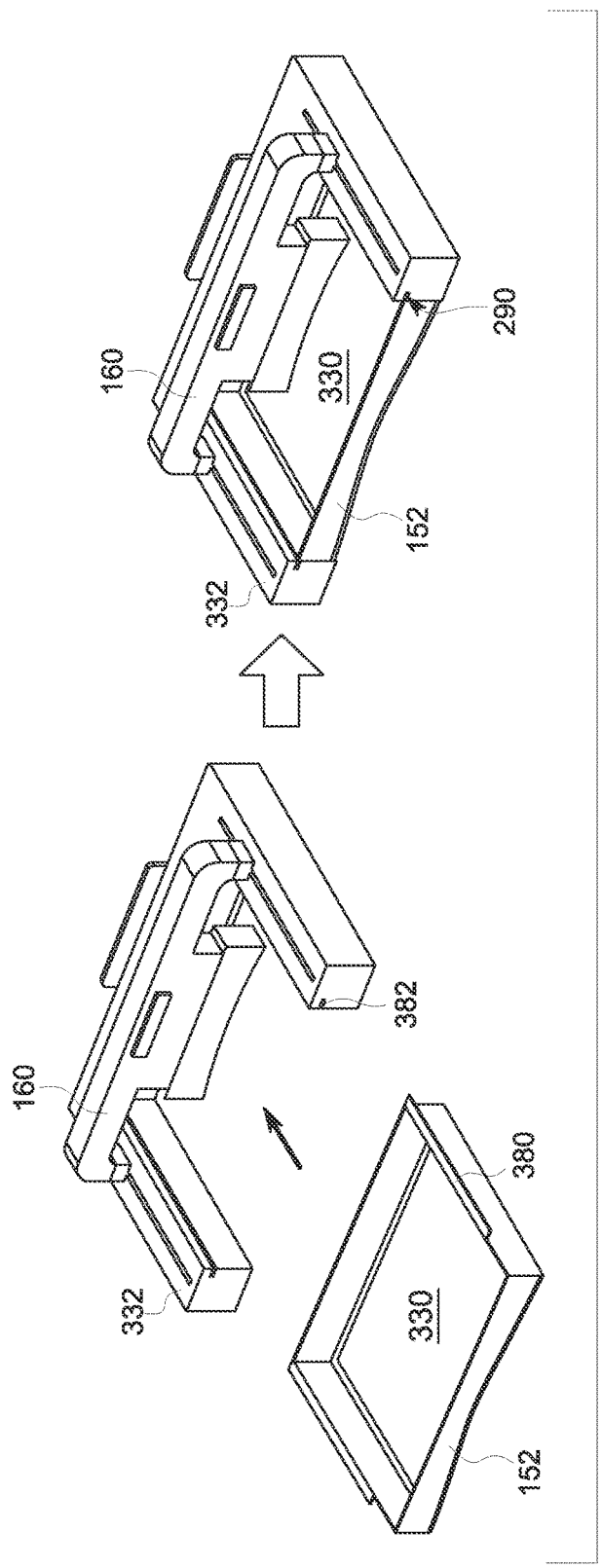
FIG. 15 depicts association of a paddle assembly with an ultrasound scan assembly, in accordance with aspects of the present disclosure.

Turning to FIG. 15, as noted herein at various points, the paddle 152, such as a mesh or other conformable paddle, may be one of a variety of such paddles, each varying by one or more of size, shape, composition, stiffness, and so forth such that a suitable paddle 152 may be selected based on a variety of patient specific factors. In addition, as noted, the paddles 152 may therefore be interchangeable with respect to the ultrasound probe assembly and corresponding frame and drive structures discussed herein. FIG. 15 depicts a sliding engagement by which a paddle 152 may be removed and/or inserted into a frame 332 on which a probe 160 is mounted. In this example, the paddle 152 includes a flange or lip structure 380 that may be fitted to an slid within a corresponding slot 382 on the frame 332 to form the sliding engagement 290 noted above. Thus, various paddles 152 may be slid in or out of the engagement 290 as needed based on imaging or patient considerations.

Technical effects of the invention include a reduced compression breast imaging system that allows for tomosynthesis and ultrasound scanning of a breast in a single compression. In certain embodiments, a system and method are provided for introducing and removing the ultrasound probe into the scan area as need, such as via a flip-up mechanism or use of a detachable ultrasound probe. One of more of positioning of the ultrasound probe, movement of the ultrasound probe, and data acquisition of the ultrasound probe may be automated or semi-automated.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A breast imaging system, comprising:
   a compression paddle comprising a non-rigid surface that is configured to contact breast tissue when in use and a rigid frame defining an outer perimeter, wherein the non-rigid surface spans an interior region defined by the outer perimeter, wherein the rigid frame comprises a front curved tissue-facing surface and a rear curved tissue-facing surface, wherein the front and rear curved tissue-facing surfaces are configured to accommodate curvature of the breast tissue when in contact, and wherein the front and rear curved tissue-facing surfaces are opposite surfaces of the rigid frame of the compression paddle;
   a frame structure comprising an open region;
   an ultrasound probe attached to the frame structure and configured to move along the frame structure over the open region during operation; and
   one or more pivot structures about which the frame structure is configured to pivot with respect to the compression paddle.

2. The breast imaging system of claim 1, wherein the frame structure further comprises one or more rails in a vertical orientation relative to the frame structure on which the ultrasound probe is mounted, wherein the ultrasound probe is biased along the one or more rails toward the breast tissue when in use but can be moved along the one or more rails against the bias.

3. The breast imaging system of claim 1, further comprising a drive rail along which the ultrasound probe moves with respect to the frame structure.

4. The breast imaging system of claim 3, further comprising a motor assembly configured to move the move the ultrasound probe along the drive rail.

5. The breast imaging system of claim 1, wherein the frame structure comprises a sliding engagement for receiving a complementary engagement structure of the compression paddle.

6. The breast imaging system of claim 1, wherein the frame structure is configured to pivot between a first position in which the ultrasound probe is not in the beam path of an X-ray source and a second position in which the ultrasound probe is positioned to acquire ultrasound image data.

7. The breast imaging system of claim 1, further comprising:
   a tomosynthesis scan system configured to acquire tomosynthesis image data when the ultrasound probe is pivoted out of the beam path of the tomosynthesis scan system.

8. The breast imaging system of claim 1, further comprising a motion controller module configured to automatically move some or all of the ultrasound probe or the frame structure during an ultrasound examination.

9. The breast imaging system of claim 1, wherein the non-rigid surface of the compression paddle comprises a mesh material.

10. The breast imaging system of claim 1, wherein the non-rigid surface of the compression paddle is at least partially conformable to the breast tissue.

11. The breast imaging system of claim 1, wherein the compression paddle, when contacting the breast tissue, is not parallel to a lower compression plate such that the compressed breast tissue is not compressed to a substantially uniform thickness.

12. The breast imaging system of claim 1, wherein the non-rigid surface comprises spaced apart radio-opaque elements.

13. The breast imaging system of claim 12, wherein the spaced apart radio-opaque elements, when imaged, correspond to a patient skin line.

14. A breast imaging system, comprising:
a compression paddle comprising a non-rigid surface that is configured to contact breast tissue when in use and a rigid frame defining an outer perimeter, wherein the non-rigid surface spans an interior region defined by the outer perimeter, wherein the rigid frame comprises a front curved tissue-facing surface and a rear curved tissue-facing surface, wherein the front and rear curved tissue-facing surfaces are configured to accommodate curvature of the breast tissue when in contact, and wherein the front and rear curved tissue-facing surfaces are opposite surfaces of the rigid frame of the compression paddle;
a frame structure comprising:
an open region overlying the non-rigid surface; and
one or more engagement structures;
a removable ultrasound probe comprising one or more complementary structures configured to engage and disengage the engagement structures, wherein the ultrasound probe is configured to move along the frame structure over the open region during operation.

15. The breast imaging system of claim 14, wherein the ultrasound probe, when engaged is movable between a retracted position and an unretracted position relative to a surface of the frame structure.

16. The breast imaging system of claim 14, further comprising:
a tomosynthesis scan system configured to acquire tomosynthesis image data when the ultrasound probe is detached form the frame structure.

17. A method for acquiring breast imaging data, comprising:
compressing breast tissue to a non-uniform thickness using a compression paddle comprising a non-rigid surface that is configured to contact the breast tissue when in use and a rigid frame defining an outer perimeter, wherein the non-rigid surface spans an interior region defined by the outer perimeter, wherein the rigid frame comprises a front curved tissue-facing surface and a rear curved tissue-facing surface, wherein the front and rear curved tissue-facing surfaces are configured to accommodate curvature of the breast tissue when in contact, and wherein the front and rear curved tissue-facing surfaces are opposite surfaces of the rigid frame of the compression paddle;
acquiring one or more tomosynthesis images of the breast tissue;
positioning an ultrasound probe on the breast tissue, wherein the ultrasound probe is positioned outside the an X-ray beam path during acquisition of the one or more tomosynthesis images and within the X-ray beam path when positioned on the breast tissue;
moving the ultrasound probe along a defined scan path;
acquiring one or more ultrasound images of the breast tissue using the ultrasound probe; and
releasing compression of the breast tissue.

18. The method of claim 17, wherein the compressing the breast tissue comprises compressing the breast tissue using a conformable mesh compression paddle.

\* \* \* \* \*